United States Patent [19]

Spitz et al.

[11] 4,215,695
[45] Aug. 5, 1980

[54] FLUID DRAINING SYSTEM

[75] Inventors: Eugene B. Spitz; Richard E. Brenz, both of Media; Charles C. Hansford, Phoenixville, all of Pa.

[73] Assignee: Medical Devices, Inc., Media, Pa.

[21] Appl. No.: 880,103

[22] Filed: Feb. 22, 1978

[51] Int. Cl.² ........................ A61M 1/00; A61M 27/00
[52] U.S. Cl. ................................. 128/350 V; 128/231
[58] Field of Search ............... 128/350 V, 350 R, 247, 128/231; 137/242

[56] References Cited

U.S. PATENT DOCUMENTS

| | | | |
|---|---|---|---|
| 2,969,066 | 1/1961 | Holter et al. | 128/350 V |
| 3,566,875 | 3/1971 | Stoehr | 128/350 V |
| 3,683,929 | 8/1972 | Holter | 128/350 V |

Primary Examiner—Stephen C. Pellegrino
Attorney, Agent, or Firm—Paul Maleson

[57] ABSTRACT

An improved cerebrospinal fluid draining system adapted for insertion into the human body in order to control fluid flow passage of the cerebrospinal fluid from an area in the vicinity of the brain to a remote point of the body. The cerebrospinal fluid drain system includes a longitudinally extended sleeve member having a through opening in fluid communication with a catheter extending into the brain area of the body. A check valve mechanism having an inlet opening is in fluid communication with the sleeve member for receiving the fluid and includes an outlet passage for egressing fluid inserted under pressure into the check valve mechanism. The check valve mechanism includes a hinge element formed at a predetermined location to allow opening of the outlet passage responsive to a predetermined fluid pressure value and to further reliably close the outlet passage when the fluid pressure is less than some predetermined value.

14 Claims, 5 Drawing Figures

U.S. Patent    Aug. 5, 1980    4,215,695
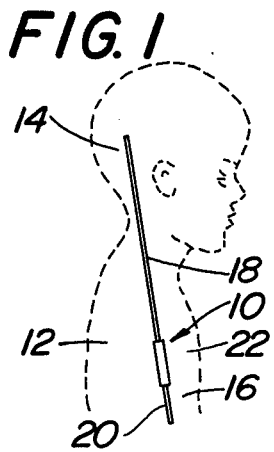
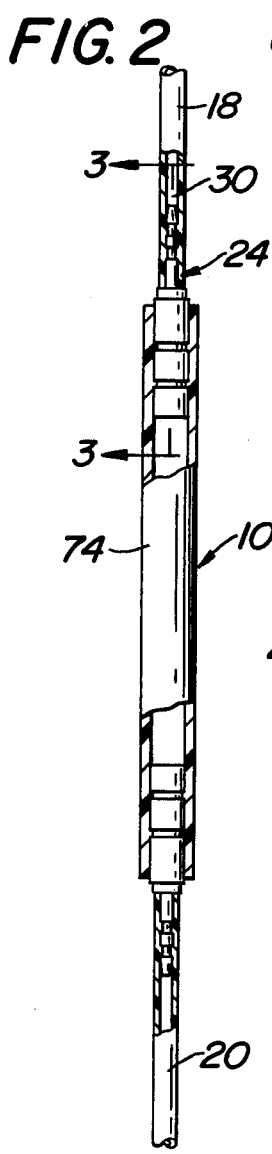
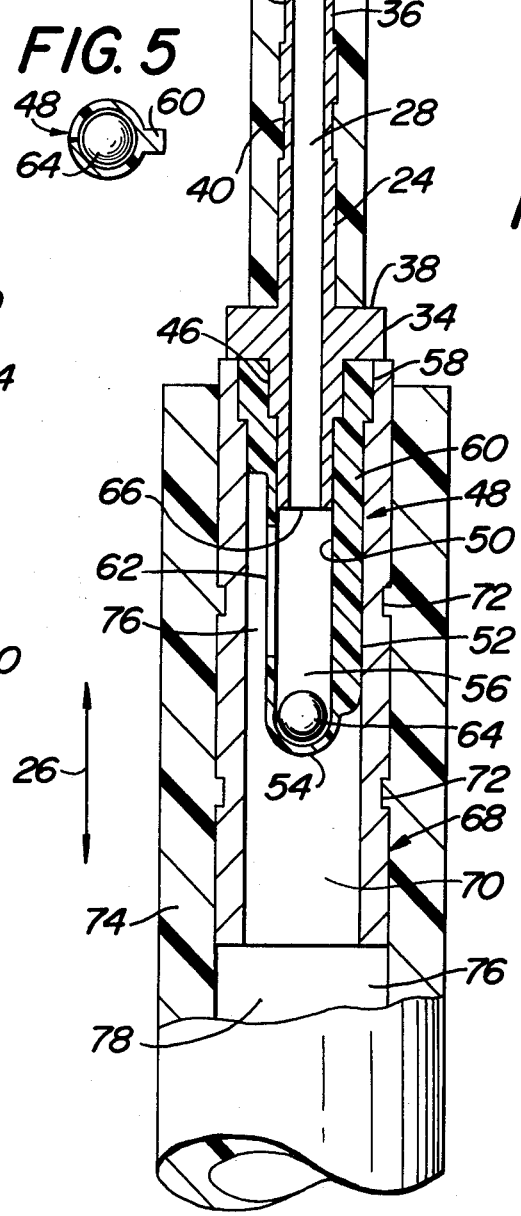
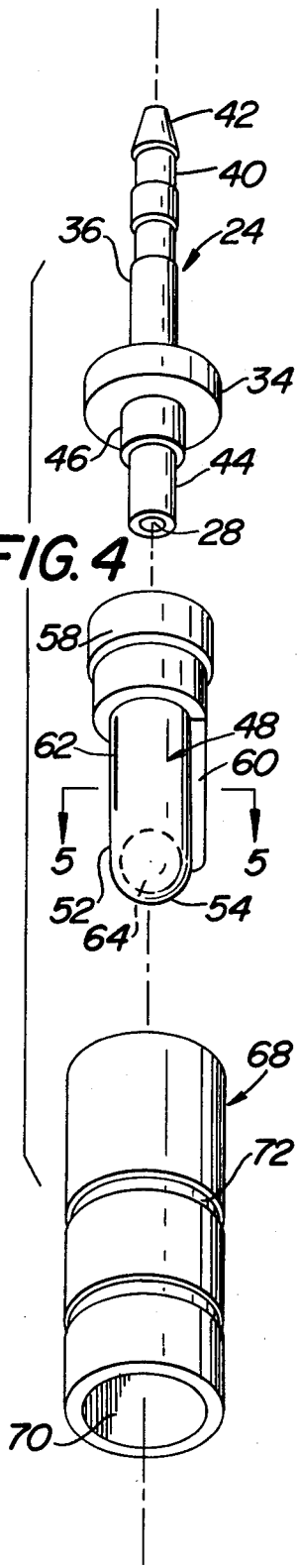

FLUID DRAINING SYSTEM

CROSS REFERENCE TO RELATED REFERENCES

This application incorporates by reference U.S. Pat. No. 3,566,875, issued Mar. 2, 1971.

BACKGROUND OF THE INVENTION

1. FIELD OF THE INVENTION

The present invention relates to medical devices implanted within the human body. The instant invention pertains to device systems being implanted within the human body for draining cerebrospinal fluid during the treatment of hydrocephallus. The subject invention pertains to an improved cerebrospinal fluid draining system including a check valve mechanism which allows passage of cerebrospinal fluid in one direction. The instant invention relates to a cerebrospinal fluid draining system having a check valve where the opening and closing of the check valve is formed about a fulcrum.

2. PRIOR ART

Systems for draining cerebrospinal fluid are known in the art. The closest prior art known to the inventors of the subject cerebrospinal fluid draining system in U.S. Pat. No. 3,566,875 of which this invention is an improvement. In this prior art system, a slit is utilized for the outlet passage from the check valve. However, upon experimentation it has been found that the dimensions of the slit are important in the control of the fluid egressing from the check valve. In the prior art draining system the slit is formed throughout substantially the elongated length of the check valve. The slit extended into the arcuate dome contour of the check valve mechanism. After experimentation it has been found that when the slit forming the outlet passage extends into the arcuate region of the substantially cylindrical dome shaped check valve, that control of the opening of the slit is diminished. Further, the slit defining the outlet passage did not reliably close when the pressure differential between and upstream area and a downstream area dropped below a predetermined level.

Additionally, the system shown in U.S. Pat. No. 3,566,875 was found to be deficient in the total closing of the outlet passage. Such prior systems did not allow for repeated total closing of the outlet passage due to the fact that there was not return closing forces applied to the check valve mechanism. This had the deleterious effect of permitting continual draining of the cerebrospinal fluid even when the pressure differential between the upstream and downstream areas was less than a predetermined amount.

SUMMARY OF THE INVENTION

An improved cerebrospinal fluid draining system in fluid communication with a catheter which includes a longitudinally extended sleeve member having a through opening in cooperative alignment with a fluid flow passage formed in the catheter. A check valve mechanism is secured to the sleeve member and has an inlet opening for receiving the fluid from the sleeve member. A hinge element is formed on the check valve mechanism for (1) opening an outlet passage formed through the check valve mechanism responsive to a predetermined fluid pressure value within the valve mechanism, and (2) closing the outlet passage when the fluid pressure is less than the predetermined value.

BRIEF DESCRIPTION OF THE DRAWINGS

FIG. 1 is a view of the improved cerebrospinal fluid draining system implanted within a human body;

FIG. 2 is an elevation view of the fluid draining system partially cut-away showing the system positionally located between an upstream and a downstream catheter;

FIG. 3 is a section view of a portion of the fluid draining system taken along the section line 3—3 of FIG. 2;

FIG. 4 is an exploded view taken in perspective of the basic elements of the improved cerebrospinal fluid draining; and, FIG. 5 is a section view of the check valve mechanism taken along the section line 5—5 of FIG. 4.

DESCRIPTION OF THE PREFERRED EMBODIMENTS

Referring now to FIGS. 1–5 there is shown cerebrospinal fluid draining system 10 adapted for insertion into human body 12. In overall concept, fluid draining system 10 is used to control fluid flow passage of cerebrospinal fluid being directed from upstream area 14 to downstream area 16 displaced from the brain area of human body 12. Cerebrospinal fluid draining system 10 is coupled to upstream catheter 18 and downstream catheter 20 to provide an appropriate fluid communication path between upstream and downstream areas 14 and 16 respectively. As will be seen in following paragraphs fluid draining system 10 forms a means whereby cerebrospinal fluid pressure differentials between upstream area 14 and downstream area 20 may be effectively controlled in order that when a positive pressure differential exists between upstream and downstream areas 14 and 16 that there is an appropriate fluid flow path created therebetween to relieve fluid pressure in the brain area of human body 12.

Generally, cerebrospinal fluid draining system 10 is positionally located within human body 12 and implanted adjacent to the outer skin of the person. System 10 has been successfully implanted in the clavicle area 22 of human body 12 with upstream catheter 18 passing to the general area of the laterial ventricles within the skull for drainage of the cerebrospinal fluid therefrom. Downstream catheter 20 of system 10 passes to some other portion of body 12 such as the peritoneal cavity to permit drainage of the fluid thereto. Positional placement of system 10 within body 12 may be affected in a number of locations and in some positional placements may be located nearer upstream area 14 than the location shown in FIG. 1 which is presented for illustration purposes only. However, specific positional placement of system 10 within body 12 is not important to the improvements in the inventive concept as is herein described.

The improvements of cerebrospinal fluid drainage system 10 over prior systems utilized for such drainage purposes is directed to the fact that prior systems have been found to have a low reliability concerning opening and closing of such drainage systems dependent on the pressure differentials existing between upstream and downstream areas 14 and 16. Prior systems have been found to open at a predetermined pressure differential ratio however, when the pressure differential ratio falls below the prescribed or predetermined point, where the system should close, such has been found in some cases to remain open thereby causing possible excessive fluid to drain from upstream area 14. This has possibly caused deleterious effects to a number of persons and thus a program for obtaining high reliability opening and closing of draining systems has resulted in the subject fluid draining system 10 being provided.

Cerebrospinal fluid draining system 10 includes sleeve member 24 extending in longitudinal direction defined by directional arrow 26. Sleeve member 24 includes through opening 28 in cooperative alignment with fluid flow passage 30 formed within upstream catheter 18. As can be seen in FIG. 3, sleeve member 24 is inserted within catheter through opening 30 in frictional securement with catheter inner wall 32.

Sleeve member 24 includes flange element 34 having a larger external diameter than longitudinally extended first portion 36. In this manner a lower section of upstream catheter 18 may be forced into abutting relation with sleeve flange upper surface 38. Sleeve member first portion 36 includes a pair of channels 40 formed around the a peripheral external wall in order to provide additional securement means to sleeve member 24 to catheter 18. In operation, a suture or other string like element is tied around catheter 18 within the channels 40. Upstream catheter 18 is resilient in composition being generally formed of a plastic like material and the suture is drawn in tightened securement in order to deform and compress catheter 18 into channels 40. Thus, channels 40 merely provide for an additional securement mechanism in order to assure securement of sleeve member 24 within catheter 18.

Sleeve first portion 36 also includes tapered end 42 to provide a guide for insert of sleeve member 28 within catheter through opening 30. Tapered end portion 42 is of importance during an operating sequence due to the fact that generally a quick and reliable insert into catheter 18 is required to minimize the overall time of placement of draining system 10 within body 12. Sleeve member 24 further includes sleeve second portion 44 having lower flange 46 to provide appropriate interface with the check valve mechanism to be described in following paragraphs.

Cerebrospinal fluid draining system 10 includes check valve mechanism 48 clearly shown in FIGS. 3 and 4. Check valve mechanism 48 includes check valve opening passage 50 for receiving fluid passing through sleeve member 24. In overall contour, check valve mechanism 48 includes longitudinally extended hollow cylindrical member 52 having dome shaped contour surface 54 formed on one end thereof. Hollow cylindrical member 52 defines internal cavity 56 for accepting fluid being drained through upstream catheter 18, sleeve member 24 and being inserted into check valve opening 50. Valve 48 further includes upper flange 58 having an internal diameter adapted to be inserted over and in frictional securement with lower sleeve flange 46.

Valve 48 further includes hinge extension member 60 formed on an outer wall of cylindrical extension 52 in order to (1) open an outlet passage formed through check valve 48 responsive to a predetermined fluid pressure value within valve 48, as well as (2) to close the outlet passage when the fluid pressure is less than the predetermined value. The outlet passage for fluids contained within valve cavity 56 is provided by slit 62 which is longitudinally extended through a side wall of check valve 48. Of importance, is the fact that the extended length in the longitudinal direction 26 of slit 62 is formed only in a portion of the side wall of check valve 48. Slit 62 is formed within the extended length of check valve 50 where such is linearly directed in longitudinal direction 26. When slit 62 has been extended into the arcuate portion of valve 48 defined by dome surface 54 it has been found that control of the opening and closing of slit 62 defining the outlet passage has been diminished to a great extent. Thus, the flow through slit 62 is a direct function of maintaining slit 62 within the linearly directed portion of cylindrical member 52 of valve 48.

Hinge element 60 is longitudinally directed and defines an extension member secured to an external surface of the side wall of cylindrical member 52. Extension member or hinge 60 is formed in opposing transverse relation to slit 62 with respect to a side wall of cylindrical member 52. Thus, slit 62 and hinge or extension meber 60 are formed on opposing transverse sides of cylindrical member 52. In this manner extension member 60 has been found to form a longitudinally directed fulcrum about which slit 62 opens and closes to form the outlet passage responsive to a predetermined fluid pressure value. The addition of extension member or hinge 60 has increased the reliability of closing slit 62 subsequent to a predetermined pressure value being reduced. Check valve 48 and associated members such as hinge element 60 are generally formed in one piece formation and are resilient in nature. One composition of check valve mechanism 48 which has been successfully used is silicone rubber however, the particular composition of check valve 48 is not important to the inventive concept as is herein defined with the exception that such be amenable for insertion into body 12 without causing detrimental effects.

Check valve mechanism 48 further includes ball member 64 which is maintained within valve cavity 56. Ball member 64 includes a diameter sufficient for blocking sleeve inlet opening 66 to prevent back flow of fluid into upstream catheter 18. Thus, sphere or ball member 64 is utilized for intercepting the path of back flow fluid responsive to a predetermined fluid pressure ratio between sleeve member 24 and internal cavity 56 of check valve mechanism 48. In this manner, even if slit 62 is slightly opened, sphere member 64 acts as a check valve element to prevent any fluid communication between downstream area 16 and upstream area 14 when the pressure ratio would define a back flow of the fluid.

Draining system 10 includes longitudinally extending casing 68 having through opening 70. As is clearly seen in FIG. 3 casing member 68 is insertable over check valve mechanism 48 and is positionally located in abutting relation with a lower surface of sleeve flange 34. Casing member 68 further includes a pair of channels 72 formed within an exterior lateral wall thereof. Channels 72 provide for relief areas where adhesive utilized to bond casing 68 to primary chamber 74 is allowed to expand. As can be seen from FIG. 3, the general overall external diameter of cylindrical member 52 of valve mechanism 48 is less than the diameter of casing through opening 70. Thus, there is a fluid flow passage 76 to allow fluid passing from valve cavity 56 to flow therethrough into casing through opening 70. Casing 68 as well as sleeve member 24 is generally formed of stainless steel composition in order to provide an inert and structurally sound portion of fluid draining system 10 when such is inserted within human body 12. Priming chamber housing 74 is extended in longitudinal direction 26 and includes through passage 76. Housing 74 is partially insertable over casing member 68 as is shown. In general adhesive is utilized to bond casing 68 to the internal surfaces of primary chamber housing 74. Housing 74 includes priming chamber 78 which is utilized as a priming area to be compressively deformed in order to initiate flow from upstream area 14 to downstream area 16 within body 12. Housing 74 is generally formed of a silicone rubber type material similar to the composition of check valve mechanism 48.

What has been described in previous paragraphs is the upstream portions of draining system 10. It will be apparent to one skilled in the art, that draining system 10 is formed with a pair of sleeve members 24, check valve mechanisms 48, and casings 68 on opposing longitudinal ends of priming chamber housing 74 as is shown in FIG. 2. The description of the aforementioned elements inserted within downstream cavity 20 are substantially identical to those previously shown and described with the exception that the orientation is in an opposing manner as provided in FIG. 2.

It is to be understood that the foregoing examples of dimensions and positional relations are used for illustration only and the control of fluid flow may be regulated over a wide range of pressures by changing certain element construction and geometries. It is apparent that while the invention has been particularly shown and described with reference to a preferred embodiment thereof, various changes in form and detail may be made therein by those skilled in the art without departing from the spirit and scope of the invention.

What is claimed is:

1. An improved cerebrospinal fluid draining system in fluid communication with a catheter comprising:
   (a) a longitudinally extended sleeve member having a through opening in cooperative alignment with a fluid flow passage formed in said catheter;
   (b) check valve means secured to said sleeve member having an inlet opening for receiving said fluid from said sleeve member; and,
   (c) hinge means formed on said check valve means for providing a support fulcrum line to stabilize said check valve means responsive to pressure changes therein in order to aid in (1) opening an outlet passage formed through said check valve means responsive to a predetermined fluid pressure value within said valve means, and (2) closing said outlet passage when said fluid pressure is less than said predetermined value, said hinge means being secured to an external surface of said check valve means.

2. The improved cerebrospinal fluid draining system as recited in claim 1 where said check valve means includes a longitudinally extended hollow cylindrical member having a dome shaped contour one end thereof, said hollow cylindrical member defining an internal cavity.

3. The improved cerebrospinal fluid draining system as recited in claim 2 where said outlet passage includes a longitudinally extended slit formed through a sidewall of said check valve means.

4. The improved cerebrospinal fluid draining system as recited in claim 3 where said slit extends in a portion of said side wall which is linearly directed in said longitudinal direction.

5. The improved cerebrospinal fluid draining system as recited in claim 4 where said hinge means includes a longtudinally directed extension member secured to an external surface of said side wall of said cylindrical member.

6. The improved cerebrospinal fluid draining system as recited in claim 5 where said extension member is formed in opposing transverse relation to said slit with respect to said side wall of said cylindrical member.

7. The improved cerebrospinal fluid draining system as recited in claim 6 where said extension member forms a longitudinally directed fulcrum about which said outlet passage opens responsive to said predetermined fluid pressure valve.

8. The improved cerebrospinal fluid draining system as recited in claim 7 including a ball member insertable within said internal cavity for blocking said inlet opening responsive to a predetermined fluid pressure ratio between said sleeve member and said internal cavity of said check valve means.

9. The improved cerebrospinal fluid draining system as recited in claim 1 where said check valve means and said hinge means are formed of a resilient material.

10. The improved cerebrospinal fluid draining system as recited in claim 9 where said check valve means and said hinge means are formed of silicone rubber.

11. The improved cerebrospinal fluid draining system as recited in claim 1 including a longitudinally extending casing having a through opening, said casing being insertable over said check valve means.

12. The improved cerebrospinal fluid draining system as recited in claim 11 where said casing is cylindrical in contour having at least one channel formed within an exterior lateral wall thereof.

13. The improved cerebrospinal fluid draining system as recited in claim 11 including a priming chamber housing having a longitudinally extending through opening, said casing being partially insertable within said priming chamber housing through opening.

14. The improved cerebrospinal fluid draining system as recited in claim 13 where said priming chamber housing is formed of a resilient material, said priming chamber housing forming a priming chamber adjacent said check valve means.

* * * * *